(12) United States Patent
Trumbo et al.

(10) Patent No.: US 11,060,956 B2
(45) Date of Patent: *Jul. 13, 2021

(54) SYSTEMS AND METHODS FOR AUTOMATION OF LOW-FLOW GROUNDWATER SAMPLING

(71) Applicant: In-Situ, Inc., Fort Collins, CO (US)

(72) Inventors: Matthew Trumbo, Fort Collins, CO (US); Benjamin Kimbell, Fort Collins, CO (US)

(73) Assignee: IN-SITU, INC., Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/777,603

(22) Filed: Jan. 30, 2020

(65) Prior Publication Data

US 2020/0240878 A1 Jul. 30, 2020

Related U.S. Application Data

(63) Continuation of application No. 16/270,345, filed on Feb. 7, 2019, now Pat. No. 10,591,389.

(Continued)

(51) Int. Cl.
*G01N 1/14* (2006.01)
*G01N 33/18* (2006.01)
*G01N 35/00* (2006.01)
*G01N 35/10* (2006.01)
*G01N 35/04* (2006.01)

(52) U.S. Cl.
CPC ........... *G01N 1/14* (2013.01); *G01N 33/1826* (2013.01); *G01N 33/1833* (2013.01);
(Continued)

(58) Field of Classification Search
CPC ........... G01N 33/1893; G01N 33/1826; G01N 33/1833; G01N 33/1846; G01N 1/14
See application file for complete search history.

(56) References Cited

U.S. PATENT DOCUMENTS 6,021,664 A 2/2000 Granato et al.
6,547,004 B2 4/2003 Last et al.
(Continued)

FOREIGN PATENT DOCUMENTS

WO WO 2017/003670 A1 1/2017

OTHER PUBLICATIONS

U.S. Appl. No. 16/270,345, filed Feb. 7, 2019.
(Continued)

*Primary Examiner* — Paul M. West
(74) *Attorney, Agent, or Firm* — Leydig, Voit & Mayer, Ltd.

(57) ABSTRACT

Provided are low flow groundwater fluid sampling systems and related methods of collecting fluid samples, including a low flow pump, flow cell, waste container and a communication device in communication with those components. In this manner, the low flow pump may be controlled to ensure a desired constant flow-rate is achieved, and a remote operator may monitor the status of fluid being pumped to the flow cell with the communication device, such as with a portable electronic device, including a smart phone. The system may alert the operator that fluid is ready to be collected for sampling, including at an off-site laboratory. Particularly useful applications are for monitoring groundwater quality and contamination.

21 Claims, 10 Drawing Sheets

Related U.S. Application Data

(60) Provisional application No. 62/627,400, filed on Feb. 7, 2018.

(52) U.S. Cl.
CPC ..... *G01N 33/1846* (2013.01); *G01N 33/1893* (2013.01); *G01N 35/00871* (2013.01); *G01N 35/1097* (2013.01); *G01N 2001/1418* (2013.01); *G01N 2035/00881* (2013.01); *G01N 2035/0441* (2013.01)

(56) References Cited

U.S. PATENT DOCUMENTS

| | | | |
|---|---|---|---|
| 9,689,855 B2 | 6/2017 | Scott et al. | |
| 9,778,180 B2 | 10/2017 | Baltz et al. | |
| 9,835,554 B2 | 12/2017 | Scott et al. | |
| 10,591,389 B2 * | 3/2020 | Trumbo | G01N 1/14 |
| 2011/0003400 A1 | 1/2011 | Halden | |
| 2015/0233884 A1 | 8/2015 | Burge | |
| 2016/0146777 A1 | 5/2016 | McKee | |
| 2017/0176183 A1 | 6/2017 | Steinback et al. | |

OTHER PUBLICATIONS

EPA EQASOP-GW4 "Low stress (low flow) purging and sampling procedure for the collection of groundwater samples from monitoring wells" Rev.4 Sep. 19, 2017 (EPA 2017).

In-Situ, Inc. "Low flow kits and accessories" available at in-situ.com/wp-content/uploads/ 2014/11/LowFlow_Kits_2017.pdf (Nov. 2015), for exemplary low-flow kits, components and accessories.

International Search Report and Written Opinion dated Apr. 30, 2019 in PCT/US2019/017069 (13 pages).

* cited by examiner

SYSTEMS AND METHODS FOR AUTOMATION OF LOW-FLOW GROUNDWATER SAMPLING

CROSS-REFERENCE TO RELATED APPLICATIONS

This application is a continuation of U.S. application Ser. No. 16/270,345, filed Feb. 7, 2019, which application claims the benefit of and priority to U.S. Provisional Patent Application No. 62/627,400 filed Feb. 7, 2018, each of which are incorporated by reference herein in their entireties.

BACKGROUND OF INVENTION

Current low-flow groundwater sampling techniques tend to require a human to manually measure drawdown, evaluate stabilization of common parameters on a water quality sonde, manually measure flow, and manually control a pump. This is a time-consuming burden on the individual, resulting in high inefficiencies, inaccurate collection protocols, and resultant decrease in sample confidence. Manual measurement and control of the various known instruments and devices associated with groundwater sampling allows only one well to be sampled at a time per operator. There is a need in the art to reliably and cost-effectively automate measurement of flow and drawdown, automate control of the pump, and combine these elements in a manner that facilitates high-throughput sample collection by a single individual for multiple sampling locations.

SUMMARY OF THE INVENTION

The systems and methods provided herein relieve the operator of the above challenges and provide automated or "hands-off" operation, requiring only setup. In fully automated employment, all that may be required is for the operator to collect a ready to transport sample upon alert that the sample is ready to be collected. The systems and methods described herein facilitate time-, labor-, and cost-efficiencies to sample and perform real-time monitoring at multiple sites, such as geographically separated wells, simultaneously. This results in a tremendous savings of effort and time. The systems and methods described and claimed herein further provide the ability to efficiently monitor groundwater contamination by at least partially automating the fluid collection process. Before fluids can be collected for subsequent analysis, including at an off-site lab having the ability to precisely quantify a range of chemical species, ranging from volatile organic compounds to inorganic metals, the fluid must be "clean". In particular, the fluid in the well should be purged in order to obtain an accurate measure of groundwater contamination and avoid measuring initial fluids that tend to build-up and store contaminants so that a reading of those samples is not a true indication of environmental groundwater contamination level. The systems and methods provided herein automate this procedure so that an operator need not be on-site adjusting pump flow-rate, calculating water parameters, and deciding when stabilization is achieved. Instead, the operator may be alerted, such as via a wireless communication to a hand-held device on the person of the operator, that sample stabilization is achieved and fluid (e.g., water) collection may begin. In this manner, significant time savings and efficiencies are achieved, even while reducing the likelihood of errors caused by operator error, including arising from tracking many water quality parameters over time to determine when sampling may occur. The systems and methods similarly free the operator from being tied to specific testing sites for specific times, thereby further increasing flexibility and efficiency.

The systems and methods may be incorporated with a wireless network enabled device (also generally referred herein is a communication device capable of receiving data from any one or more components of the system), thereby providing a convenient platform for remotely reviewing flow-rate, drawdown, pump status, and any other parameters of interest. Accordingly, any of the low flow pumps may be a Bluetooth enabled pump, for instance, thereby facilitating wireless communication and control.

The systems and methods may be used with any of a range of water quality sondes, including any of the sensors and/or multiparameter sondes described in U.S. Pat. No. 9,689,855 (describing multiparameter sondes), U.S. Pat. No. 9,835,554 (describing conductivity sensors), U.S. Pat. No. 9,778,180 (describing turbidity sensors as part of the flow cell), each of which are incorporated by reference in their entirety to the extent not inconsistent herewith.

Any of the systems and methods may incorporate auto-calibration of the sensors, run stabilization routines, and sample auto-collection. Notification may be automatically sent as an alert that the samples are ready for pickup and/or waste water is ready to be disposed of. A mobile app may interface with the water quality sonde (e.g., sensors) to automatically calculate stabilization and collect other pieces of information.

Provided herein are low flow groundwater fluid sampling systems. The system may comprise: a low flow pump; a flow cell in fluid and/or electronic communication with the low flow pump, wherein the flow cell comprises one or more fluid quality sensors; a waste container in fluid communication with the flow cell for collecting a waste fluid, wherein the waste container comprises a level sensor for measuring a waste fluid depth in the waste container; a communication device in wireless communication with each of the pump, flow cell and waste container, wherein the low flow pump has an adjustable pump power to provide a desired constant flow-rate to the flow cell from the electronic communication between the low flow pump and the level sensor and the at least one fluid quality sensor measures one or more fluid parameters over a time course to assess fluid stabilization status; upon fluid stabilization the communication device indicates an affirmative fluid stabilization condition and that a fluid sample may be collected; and all fluid provided to the flow cell by the low flow pump is either collected in a fluid sample or directed to the waste container and collected as the waste fluid.

The systems provided herein are compatible with any of a range of flow sensors incorporated or positioned anywhere in the system, so long as a flow-rate can be determined and used to control pump power so as to maintain a desired flow-rate through the system. For example, the waste container level sensor itself can be used as a type of flow sensor, wherein the change in volume of waste fluid as a function of time provides a measure of flow-rate for controlling the adjustable pump power. Similarly, a separate flow sensor may be used upstream from the flow cell, downstream from the flow cell, or within the flow cell, to provide a measure of flow-rate used to control or adjust pump power, so as to maintain a desired, substantially constant, flow-rate.

Accordingly, any of the systems may further comprise a flow sensor in fluid and electronic communication with the low flow pump.

The system may further comprise an autosampler in fluid communication with the flow cell, wherein an output flow from the flow cell for an affirmative fluid stabilization condition is directed to the autosampler for collection. In this manner, an operator need not be physically on-site in order to collect a fluid sample. Instead, an operator or other individual, when convenient, can go to the site and pick-up the samples from the collector for subsequent off-site transport.

The flow cell may comprise a multi-parameter sonde having a plurality of fluid quality sensors. In this manner, a plurality of fluid parameters may be monitored, thereby providing improved liquid assessment fidelity and assurance that an affirmative fluid stabilization condition is reached. Fluid quality sensors include any one or more selected from the group consisting of: a turbidity sensor, a pressure sensor, a temperature sensor, an electrical conductivity sensor, a pH sensor, an electrochemical sensor such as an oxidation reduction potential (ORP) sensor, a fluorescence sensor, and any combination thereof.

Any of the systems may further comprise a depth sensor for assessing fluid draw-down level in a monitoring well, wherein the depth sensor is: in wireless communication with the communication device; electronic communication with the pump; or in communication with both.

Any of the flow cells provided herein may further comprise an auto-calibrator for automatically calibrating the one or more fluid quality sensors. For example, the auto-calibrator may have calibrated solutions with a known fluid parameter magnitude, including different solutions spanning a range of fluid parameter magnitudes, with automated introduction of calibration solutions to provide a type of calibration curve to calibrate the sensor over a range of values prior to introduction/of groundwater. Alternatively, the flow cell may be calibrated before being used in any of the processes described herein. Accordingly, for a collected fluid sample, a wide range of fluid quality parameters may be reliably measured for the fluid sample.

The systems and methods provided herein are compatible with a range of flow-rates, depending on the application of interest, such as related flow characteristics in and around a test well. For example, the desired or constant flow-rate may be greater than or equal to 1 mL/min and less than or equal to 500 mL/min.

The waste container level sensor may comprise a pressure transducer at a bottom surface of the waste container to measure waste fluid level in the waste container. Other examples include optical-type sensors that optically measure a path length or change in an optical property, thereby detecting fluid level. With a waste fluid height detected, the volume is determined for a known cross-sectional area of the waste container. A mass sensor may be used to measure the mass of liquid provided to the waste container, so that for a known liquid density, flow-rate is readily determined.

In any of the systems provided herein, one or more of a fluid flow-rate or a water well depth is transmitted to the communication device and a control signal is transmitted from the communication device to the low flow pump to maintain the desired or constant fluid flow-rate and/or a water well depth.

In any of the systems provided herein, a measured waste fluid depth may be wirelessly transmitted to the communication device. The communication device may then provide an alert to a user, such as a waste fluid alarm for a waste fluid depth that is greater than or equal to a waste fluid depth maximum. In this manner, overfilling of the waste fluid container is avoided. The waste fluid depth maximum may be less than the depth of the waste container, so as to provide time to an operator before the container overfills and to provide the ability to handle the waste container without spilling. For example, the waste fluid depth maximum may correspond to about 75% to 100% of the waste container depth, such as between 75% and 95%, and any sub-ranges thereof.

The communication device may comprises a mobile smartphone, a handheld portable device, or a computer.

The communication device may comprise a telemetry system positioned for transmitting data to a mobile device or a remote monitoring station.

The systems provided herein can be part of a multiplexed system comprising a plurality of the low flow groundwater sampling systems for simultaneously monitoring of a plurality groundwater wells. In this manner, one operator may manage and monitor fluid collection substantially simultaneously over a wide geographic range.

The systems provided herein are compatible with a range of applications, including for use in a groundwater contamination application, wherein a clean fluid sample is used for off-site testing of said clean fluid sample. Clean refers to a sample that has been appropriately validated as being in an affirmative fluid stabilization condition, as determined by the sensors in the flow-cell.

The groundwater contamination application may further comprise monitoring oil or gas, or byproducts thereof, for groundwater contamination.

Also provided herein are methods for collecting fluid samples using any of the systems described herein.

For example, a method for collecting low flow fluid samples from groundwater may comprise the steps of: continuously pumping a flow of groundwater fluid to a flow cell at a substantially constant flow-rate; measuring a fluid quality parameter time course with a fluid sensor in said flow cell; identifying a positive fluid quality stabilization status for said measured fluid quality parameter that reaches a steady-state value; and wirelessly transmitting a signal to a communication device indicating a fluid sample is ready to be collected from said flow of groundwater fluid.

The method may further comprise the step of manually collecting the fluid sample after the fluid stabilization is achieved.

The method may further comprise the steps of collecting a waste fluid that exits said flow cell in a waste container; and monitoring a waste fluid level with a level sensor connected to the waste container.

Any of the methods may be used with an autosampler, such as by activating an autosampler to automatically collect fluid sample that exits the flow cell after the positive or affirmative fluid quality stabilization status is identified.

The method may be used for simultaneous collection of a plurality of low flow fluid samples from a plurality of wells, such as by a multiplexed connection of a plurality of the systems described herein, with one system provided per well.

The continuously pumping may be by a low-flow pump fluidly connected or in fluid contact with a sample well.

The sample well may be configured to monitor contamination of ground water, including oil or gas contamination, heavy metal contamination, solvent contamination, or contamination of a material from an industrial process.

Any of the methods may further comprise the step of auto-calibrating the fluid sensor before the measuring step by: flushing the flow cell with a clean fluid, such as water; filling the flow cell with a calibration solution; measuring a calibration fluid quality parameter with the fluid sensor until stability is reached; calculating a new calibration coefficient for the fluid sensor; storing the new calibration coefficient for a subsequent fluid test measurement; and repeating until all water quality parameters for all fluid sensors are calibrated.

The continuously pumping may be automated or semi-automated by measuring fluid flow through said flow cell and/or measuring a fluid depth in a sample well, wherein the measured fluid flow and/or fluid depth generates an output that is provided as an input to said low flow pump to control pump power, thereby controlling fluid flow in a feedback loop so as to maintain constant flow-rate and/or fluid depth in said sample well.

Provided herein are various low flow groundwater fluid sampling systems, including those comprising: a low flow pump; a flow cell in fluidic and electronic communication with said low flow pump, wherein said flow cell comprises one or more fluid quality sensors; a waste container in fluid communication with said flow cell for collecting a waste fluid, wherein said waste container comprises a level sensor for measuring a waste fluid depth in said waste container; an autosampler in fluid communication with said flow cell, wherein an output flow from said flow cell for said affirmative fluid stabilization condition is directed to said autosampler for collection, wherein: a communication device is in communication, including wireless communication, with each of said pump, flow cell and waste container; said pump has an adjustable pump power to provide a desired constant flow-rate to said flow cell from said electronic communication between said low flow pump and said flow sensor and said at least one fluid quality sensor measures at least one or more fluid parameters over a time course to assess fluid stabilization status; upon fluid stabilization said communication device actuates said autosampler to collect a fluid sample; all fluid provided to said flow cell is either collected in a fluid sample or directed to said waste container and collected as said waste fluid; and said communication device is configured to generate a sample ready signal to a user or operator upon collection of said fluid sample. In this manner, all that is required of the user or operator is to collect the fluid sample for transport to an off-site testing facility.

Any of the systems may comprise a sampling controller for implementing any of the control schemes described herein. For example, the sampling controller may be part of, or operably connected to, the communication device.

Also provided are systems for sampling or monitoring groundwater, optionally under low-flow conditions, the system comprising: a flow cell including at least one fluid quality sensor; a pump in flow communication with the flow cell; a flow sensor in flow communication with the flow cell; a pump controller for regulating a fluid flow-rate from a groundwater source to the flow cell, the pump controller operatively coupled to the pump; and a sampling controller for implementing a control scheme for the groundwater sampling system, the sampling controller communicatively coupled to: the flow sensor, the at least one fluid quality sensor, and the pump controller. The control scheme may include: (a) transmitting a control signal to the pump controller in response to signals received from the flow sensor to facilitate maintaining a substantially constant fluid flow-rate from the groundwater source to the flow cell; (b) determining one or more fluid parameters over a time course based on signals received from the at least one fluid quality sensor; (c) determining a fluid stabilization status of groundwater flowed to the flow cell by the pump based on the one or more fluid parameters determined in (b); and (d) in response to an affirmative fluid stabilization condition being determined in (c), initiating collection of at least one fluid sample of the groundwater under test. As described, the collection may be into a sample container for subsequent transport and testing in an off-site testing facility. The collection may be automated or manual.

Any of the systems described herein optionally include a waste container in flow communication with the flow cell, wherein the flow sensor is a depth sensor positioned in the waste container configured to measure the amount of waste fluid collected in the waste container. In this manner, the flow-rate is determined by the change in the volume of waste fluid with time, thereby avoiding a need for a separate flow sensor. Of course, any of the systems and methods described herein are compatible with one or more flow sensors positioned at distinct locations, such as upstream and/or downstream of the flow cell, or within the flow cell itself, to provide additional monitoring capability, quality control and troubleshooting. Similarly, any one or more additional flow components may be utilized, such as filters, pressure sensors, valves, and the like. A filter is optionally utilized near an inlet to the system, to further minimize risk of clogging and fouling.

The flow sensor may be positioned upstream of an inlet of the flow cell; the fluid flow-rate from the groundwater source to the flow cell is a first fluid flow-rate of the groundwater under test into the inlet; the system may further comprise an outlet flow sensor for measuring a second flow-rate of the groundwater under test out of an outlet of the flow cell, the outlet flow sensor positioned proximal the outlet and communicatively coupled to the sampling controller; and the control scheme further includes: (e) comparing a measured value of the second flow-rate to a measured value of the first flow-rate to determine a difference therebetween.

The system may further comprise a waste container in flow communication with the flow cell for collecting a waste fluid; a first valve positioned upstream of the inlet and in flow communication with the pump, the flow cell, and the waste container; and a first valve controller for alternately directing flow of groundwater from the groundwater source to one of at least two flow paths, the first valve controller operatively coupled to the first valve, the at least two flow paths including: a first flow path from the pump to the flow cell, and a second flow path from the pump to the waste container.

The control scheme may further include: (f) in response to a value of the difference determined in (e) being greater than or equal to a predetermined flow-rate difference, transmitting a control signal to the first valve controller to facilitate diverting the flow of groundwater from the pump to the second flow path.

The system may further comprise: a second valve positioned downstream of the outlet and in flow communication with the flow cell and the waste container; and a second valve controller for alternately opening and closing the second valve to facilitate alternately starting and stopping, respectively, flow of groundwater into or out of the outlet, the second valve controller operatively coupled to the second valve.

The control scheme may further include: (g) in response to a value of the difference determined in (e) being greater than or equal to a predetermined flow-rate difference, transmitting a control signal to the second valve controller to facilitate closing the second valve and stopping flow of groundwater into the outlet.

The system may further comprise: a waste container in flow communication with the flow cell for collecting a waste fluid; a second valve positioned downstream of the outlet and in flow communication with the flow cell and the waste container; and a second valve controller for alternately directing flow of groundwater from the flow cell to one of at least two flow paths, the second valve controller operatively coupled to the second valve, the at least two flow paths including: a first flow path from the flow cell to the at least one fluid sample, and a second flow path from the flow cell to the waste container.

The control scheme may further include: (i) transmitting a control signal to the second valve controller to facilitate diverting the groundwater under test to the first flow path to further facilitate collecting the at least one fluid sample.

Any of the systems may further comprise an autosampler for collecting a plurality of fluid samples, the autosampler including: a sample platform, and an electric motor operatively coupled to the sample platform, and a motor controller operatively coupled to the motor, the motor controller communicatively coupled to the sampling controller, and wherein, for (d), with the control scheme further including: (i) for at least one iteration: transmitting a control signal to the motor controller to facilitate incrementally moving the sample platform from a position of a first container for containing a first fluid sample to at least a second container for containing at least a second fluid sample.

The at least one of: the flow sensor, the at least one fluid quality sensor, and the pump controller, may be wirelessly communicatively coupled to the sampling controller.

The at least one fluid quality sensor may include at least one of: a turbidity sensor, a pressure sensor, a temperature sensor, a dissolved oxygen sensor, an oxidation reduction potential sensor, and a fluorescence sensor.

The sampling controller may comprise a computing device, the computing device including: a processor, and memory communicatively coupled to the processor; and the computing device implements the control scheme for the system.

The memory device may include a non-transitory computer readable medium storing processor-executable instructions encoded as software, which, when executed by the processor, cause the processor to implement the control scheme for the system.

The flow sensor, the at least one fluid quality sensor, and the pump controller, may be wirelessly communicatively coupled to the computing device.

The computing device may be a mobile device, such as a smartphone; and the software includes a smartphone app. In this manner, an operator may be untethered to a specific location, and can conveniently move about the day, wherein in conventional systems, substantial time was devoted to being onsite to control the process and ensure appropriate samples were collected.

Any of the systems and methods may comprise an autosampler, such as an autosampler having: a sample platform, and an electric motor operatively coupled to the sample platform, and a motor controller operatively coupled to the motor, the motor controller communicatively coupled to the sampling controller. The control scheme may further include: for at least one iteration: transmitting a control signal to the motor controller to facilitate incrementally moving the sample platform from a position of a first container for containing a first fluid sample to at least a second container for containing at least a second fluid sample. In this manner, fluid samples may be periodically collected and ready for pick-up and transport to a testing facility.

Also provided is a method for monitoring groundwater comprising: (A) flowing, by a pump operatively coupled to a pump controller, groundwater under test from a groundwater source to a flow cell in flow communication with the pump, the flow cell including at least one fluid quality sensor; (B) collecting at least one fluid sample of the groundwater under test from an output flow of the flow cell; and (C) controlling, by a sampling controller, the pump controller to facilitate regulating a fluid flow-rate from a groundwater source to the flow cell, wherein the sampling controller is communicatively coupled the pump controller and communicatively coupled to a flow sensor positioned upstream of the flow cell and positioned downstream of the pump, the controlling step comprising: (i) transmitting, by the sampling controller, a control signal to a pump controller in response to signals received from the flow sensor to facilitate maintaining a substantially constant fluid flow-rate from the groundwater source to the flow cell; (ii) determining one or more fluid parameters of the groundwater under test over a time course based on signals received from the at least one fluid quality sensor; (iii) determining a fluid stabilization status of the groundwater under test based on the one or more fluid stabilization parameters determined in (ii); and (iv) in response to an affirmative fluid stabilization condition being determined in (iii), initiating collections of at least one fluid sample of the groundwater under test.

The flow sensor may be a first flow sensor positioned upstream of an inlet of the flow cell; the fluid flow-rate from the groundwater source to the flow cell is a first fluid flow-rate of the groundwater under test into the inlet; wherein the system further comprises an outlet flow sensor for measuring a second flow-rate of the groundwater under test out of an outlet of the flow cell, the outlet flow sensor positioned downstream of the first flow sensor and proximal the outlet, the outlet flow sensor communicatively coupled to the sampling controller; and the controlling step further comprises: (v) receiving signals from the outlet flow sensor for measuring a second flow-rate of the groundwater under test out of an outlet of the flow cell; and (vi) comparing a measured value of the second flow-rate to a measured value of the first flow-rate to determine a difference therebetween.

The controlling step may further comprise: (vii) in response to a value of the difference determined in (vi) being greater than or equal to a predetermined flow-rate difference, transmitting a control signal to the pump controller to facilitate at least one of: stopping operation of pump, decreasing the first flow-rate.

The controlling step may further comprise: (v) receiving signals from a waste container sensor for measuring a waste fluid depth of a waste container in flow communication with the flow cell for collecting a waste fluid, wherein the waste container sensor is positioned in the waste container, and wherein the waste container sensor is communicatively coupled to the sampling controller; (vi) determining a value of the waste fluid depth based on the signals received from the waste container sensor; and (vii) in response to the waste fluid depth value determined in (vi) being greater than or equal to a predetermined waste depth value, at least one of: a) transmitting a control signal to the pump controller to facilitate stopping operation of pump or decreasing the fluid flow-rate; and b) providing an alarm.

The collecting step may further include collecting a plurality of fluid samples of the groundwater under test using an autosampler.

Also provided herein are systems for performing any of the methods described herein.

Also provided herein is a non-transitory computer readable medium storing processor-executable instructions for implementing a control scheme of a groundwater sampling or monitoring system, which, when executed by a processor of the groundwater sampling or monitoring system, cause the processor to: flow, by a pump operatively coupled to a pump controller, groundwater under test from a groundwater source to a flow cell including at least one fluid quality sensor, wherein the pump controller, the at least one fluid quality sensor, and a flow sensor positioned upstream of the flow cell and downstream of the pump are communicatively coupled to the processor; collect at least one fluid sample of the groundwater under test from an output flow of the flow cell; and control the pump controller to facilitate regulating a fluid flow-rate from the groundwater source to the flow cell, wherein, when executed by the processor to control the pump controller, the processor-executable instructions further cause the processor to: (i) transmit a control signal to a pump controller in response to signals received from the flow sensor to facilitate maintaining a desired or constant fluid flow-rate from the groundwater source to the flow cell; (ii) determine one or more fluid parameters over a time course based on signals received from the at least one fluid quality sensor; (iii) determine a fluid stabilization status of groundwater flowed to the flow cell by the pump based on the one or more fluid stabilization parameters determined in (ii); and (iv) in response to an affirmative fluid stabilization condition being determined in (iii), initiate collection of at least one fluid sample of the groundwater under test.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1:
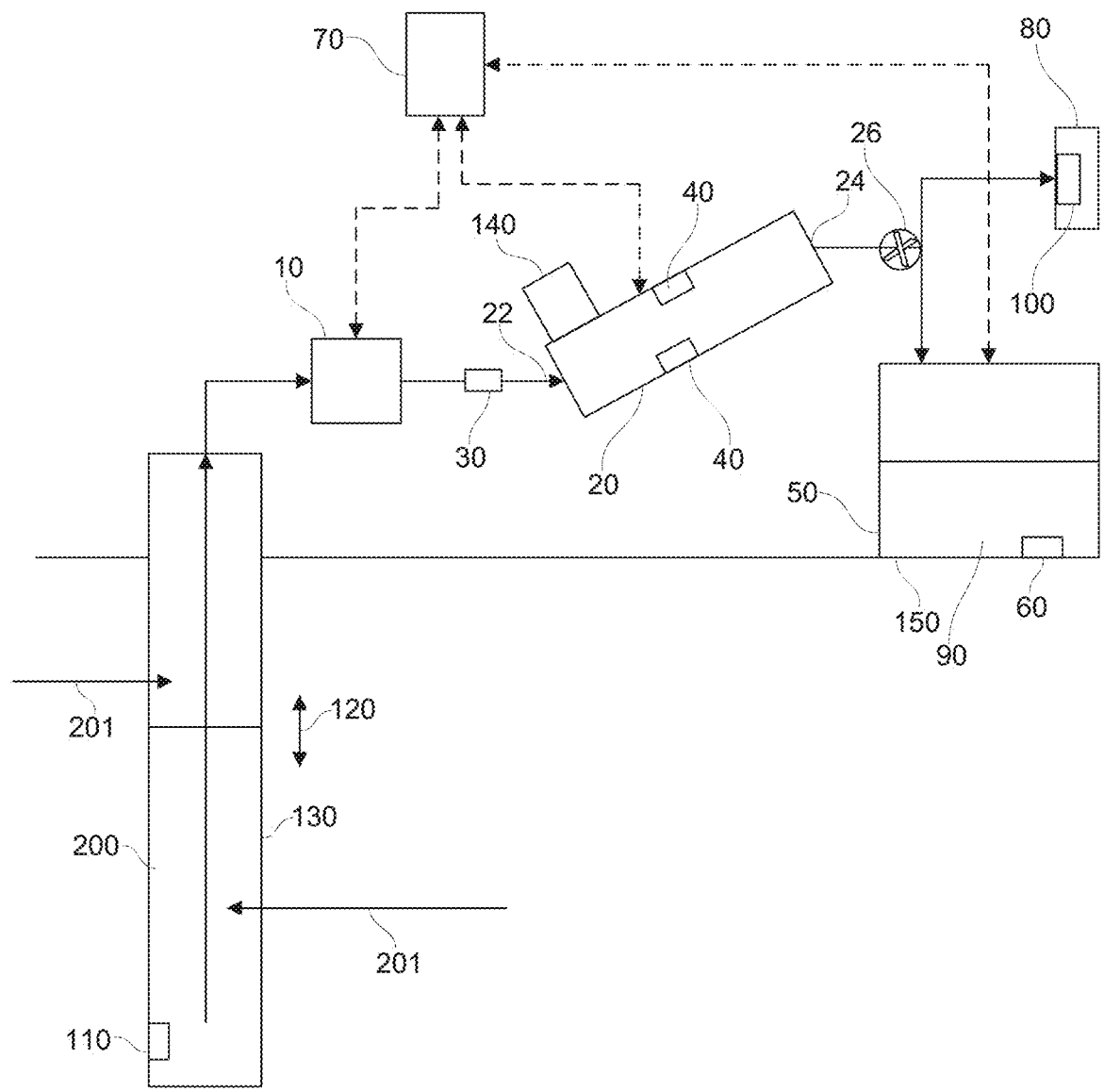
FIG. 1 is a schematic illustration of a low flow groundwater fluid sampling system.

In general, the terms and phrases used herein have their art-recognized meaning, which can be found by reference to standard texts, journal references and contexts known to those skilled in the art. The following definitions are provided to clarify their specific use in the context of the invention.

"Low flow groundwater" refers to water samples that reflect total mobile organic and inorganic loads that are transported through the subsurface under ambient flow conditions. Typical applications herein that rely on low flow groundwater are monitoring wells that are drilled for the purpose of monitoring contamination, including contaminants associated with the oil and gas industry or, more generally, any chemical manufacturing or processing application. Accordingly, the monitoring well may be anywhere oil and gas is commercially present, including production sites, storage sites, gas stations, transportation (e.g., pipelines), manufacturing, refining, and the like. Of course, the systems and methods provided herein are versatile, and may be incorporated and located for any of a range of applications where fluid (liquid) sampling is desired for subsequent off-site analysis, such as in a testing facility having instrumentation, sensitivity and/or cost-efficiency not readily available in the field.

"Low flow pump" is used broadly to refer to pumps that are designed to provide relatively low flow-rates, such as less than 1 L/min, or between 1 mL/min to 500 mL/min. The actual flow-rate range is selected so as to ensure there is minimal disturbance of the well to minimize unwanted particulate mixing with the water that has naturally flowed to the monitoring well, resulting in unwanted effects including on turbidity measurement. In addition, the low flow-rates maintain low water-level drawdowns. A low and steady flow-rate generated by the low-flow pump allows for monitoring of water parameters in order to determine when sampling may begin. Any of a range of pumps, such as adjustable rate, peristaltic, submersible, centrifugal, bladder and the like may be used. The pump may be placed downhole and configured to be submersed in water. Alternatively, the pump may be placed out of the water, with tubing provided between the water and pump for steady withdrawal of water. The pump may be adjusted to ensure there is minimal water level drawdown in the well, such as less than about 0.3 feet, or a draw down level that remains constant or substantially constant.

The samples that are properly collected are suitable for analysis of groundwater contaminants such as volatile and semi-volatile organic analytes, dissolved gases, pesticides, PCBs, metals, other inorganics of interest or naturally occurring analytes. The collected samples may be transported to a testing facility for precise testing of any one or more materials, including to assess groundwater contamination. Preferably the pump is made of a material, or has a coating, so that there is minimal leaching for pumps that are submersed in the water, thereby minimizing risk of unwanted self-contamination.

"Desired constant flow-rate" refers to a user-determined flow-rate that will result in good purging and subsequent suitable fluid for collection and subsequent sampling. Preferably, the desired constant flow-rate is selected so that there is not an undue fluid drawdown from the well and that the natural inflow of water balances the fluid pumped out of the well. Typical flow-rate values are less than 1 L/min, such as between 1 mL/min and 500 mL/min. Accordingly, the desired constant flow-rate may be greater than or equal to 1 mL/min and less than or equal to 500 mL/min, or any subranges thereof. "Constant", in this context, is used broadly and refers to the goal that flow-rate remains relatively steady, recognizing it is not practical, especially in the field, to achieve an exact non-deviating constant. Instead, practical realities such as related to fluid level fluctuations, pump power fluctuations, obstructions, disturbances and any of a variety of other external factors, will result in some deviation from constant. Accordingly, desired constant flow-rate may refer to a time-averaged flow-rate with a standard deviation or, more simply a maximum deviation, that is within 20%, 10% or 5% of the mean or desired flow-rate. If the measured flow-rate then falls outside such a standard deviation or has a maximum deviation outside of 20%, 10% or 5%, the flow may be considered not constant, and the system continues to pump until a sufficient duration of a desired constant flow-rate is achieved. That duration may be selected as greater than or equal to 1 minute, 5 minutes, 15 minutes, 30 minutes, or 1 hour. In this aspect, "constant flow-rate" may be used interchangeably with "substantially constant flow-rate" to reflect there is some tolerance in sample collection to minor variations in flow-rate, such as a mean flow-rate with a standard deviation that is within 20%, 10% or 5% of the mean flow-rate or a maximum deviation that is within 20%, 10% or 5% of the mean or desired flow-rate.

The "flow cell" directs pumped fluid over one or more "fluid quality sensors". As discussed, any one or more of the sensors or sondes, including a multiparameter sonde, of U.S. application Ser. No. 16/251,651 ("Fast Response Temperature Sensors" filed Jan. 18, 2019, U.S. Pub. Nos. 2017/0176183, 2016/0146777; and U.S. Pat. Nos. 9,689,855; 9,778,180, D755,655, are incorporated by reference, including for use in flow cells or any other position where a liquid parameter is desirably measured. See also, In-Situ, Inc. "Low flow kits and accessories" available at in-situ.com/wp-content/uploads/2014/11/LowFlow_Kits_2017.pdf (November 2015), for exemplary low-flow kits, components and accessories.

"Steady-state" or "stabilization" refers to one or more fluid quality sensors achieving a stable read-out of the one or more water quality parameters. Examples of fluid quality sensors include turbidity, temperature, specific conductance, pH, oxidation-reduction potential (ORP), and dissolved oxygen (DO). Stabilization can be defined by a user or may be a rule or regulation implemented by a government agency or standard setting body, and generally refers to multiple consecutive measurements that have a substantially constant measured water quality parameter. The invention is compatible with any number or types of stabilization definitions. For example, stabilization may refer to a deviation, such as maximum deviation, standard deviation, or the like, over a number of consecutive measurements or a time frame, such as three or more consecutive measurements or a time period that is greater than a user-specified amount. The specific definition of stabilization can be from a regulation, such as US EPA EQASOP-GW4 "Low stress (low flow) purging and sampling procedure for the collection of groundwater samples from monitoring wells" Rev. 4 Sep. 19, 2017 (EPA 2017). For example: "Stabilization is considered to be achieved when three consecutive readings are within the following limits: Turbidity (10% for values greater than 5 NTU; if three Turbidity values are less than 5 NTU, consider the values as stabilized), Dissolved Oxygen (10% for values greater than 0.5 mg/L, if three Dissolved; Oxygen values are less than 0.5 mg/L, consider the values as stabilized), Specific Conductance (3%), Temperature (3%), pH (±0.1 unit), Oxidation/Reduction Potential (±10 millivolts)." EPA 2017 is specifically incorporated by reference herein, including for the various definitions of "stability" for the different liquid quality parameters.

Whether the measurement has achieved "stability" or is "stable" depends, at least in part, on the sensitivity, reliability and reproducibility of the underlying sensor, as well as the particular application and corresponding liquid quality characteristics. For example, fluids having high turbidity may have a higher variability in measurements than lower turbidity. Stability may be considered achieved for turbidity variation of less than 10%, dissolved oxygen of less than 10%, specific conductance of less than 3%, temperature of less than 3%, pH variation of less than 0.1, and/or ORP variation of less than 10 mV. The variation may be calculated for three or more consecutive readings, including readings that are separated by at least one full fluid volume turnover of the flow cell.

"Communication device" is used broadly herein to refer to a component or device that is capable of receiving and/or transmitting signals. Accordingly, a communication device can be a type of controller, a display, a computer or processer that receives signals, processes them, and sends commands, such as pump power command, valve control, sampling, collection, waste level action, and the like. The communication device can comprise a portable device or a work station, including that is being used by the operator to monitor the systems and, as appropriate, collect samples or over-ride the system.

"Operably connected" or "operatively coupled" refers to a configuration of elements, wherein an action or reaction of one element affects another element, but in a manner that preserves each element's functionality. For example, any of the controllers provided herein may be described as being operatively coupled to another component whose signal is used to control at least a portion of the system, such as pump power, flow direction, sample collection, or a signal sent to, or received by, an operator or an electronic device used by an operator.

"Fluid communication" refers to components that are connected by fluid flow, but in a manner that does not affect either component's functionality. The connection may be direct, where a flow from an output of one component is provided as an input to another component. The connection may be indirect, where an intervening component is positioned between the components.

Example 1: Low-Flow Groundwater Sampling System

Figure 2:
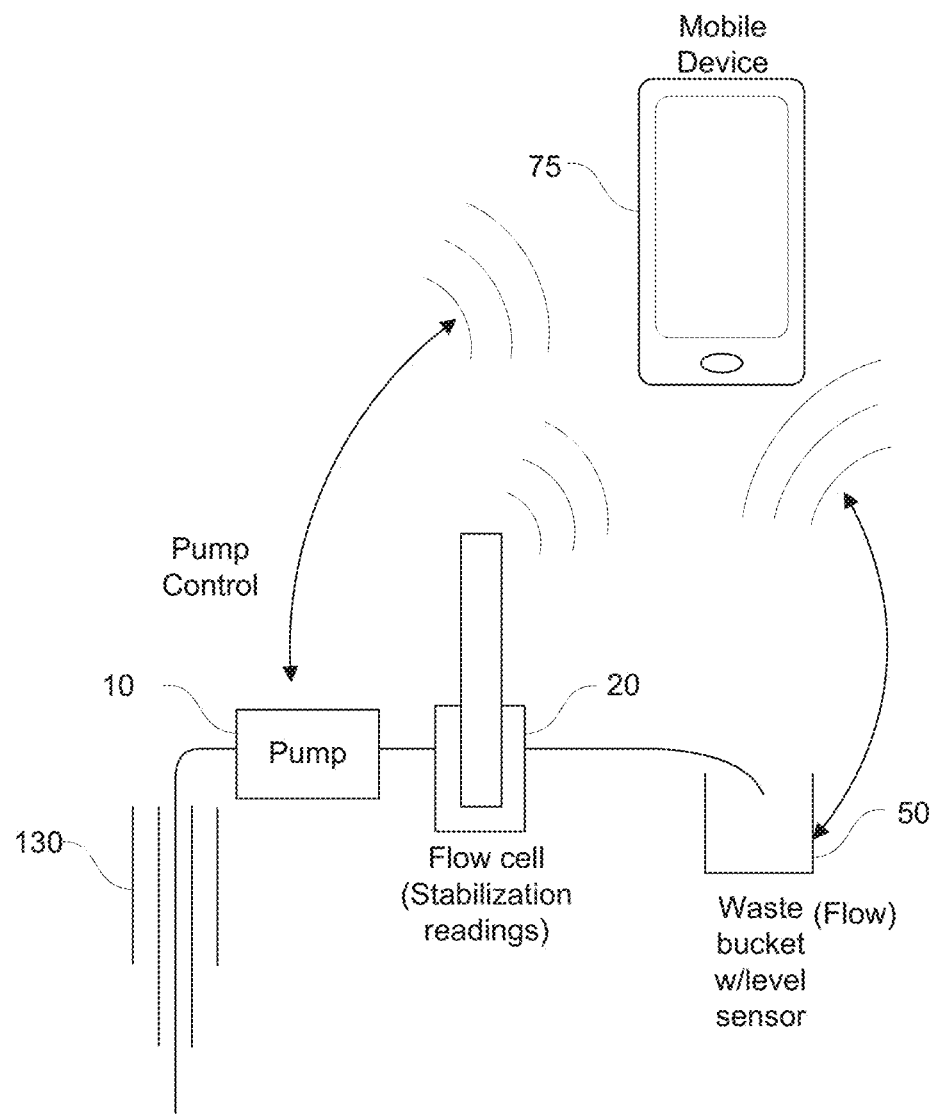
FIG. 2 is a schematic illustration of a low flow groundwater fluid sampling system with a mobile device as a communication device.
Figure 3:
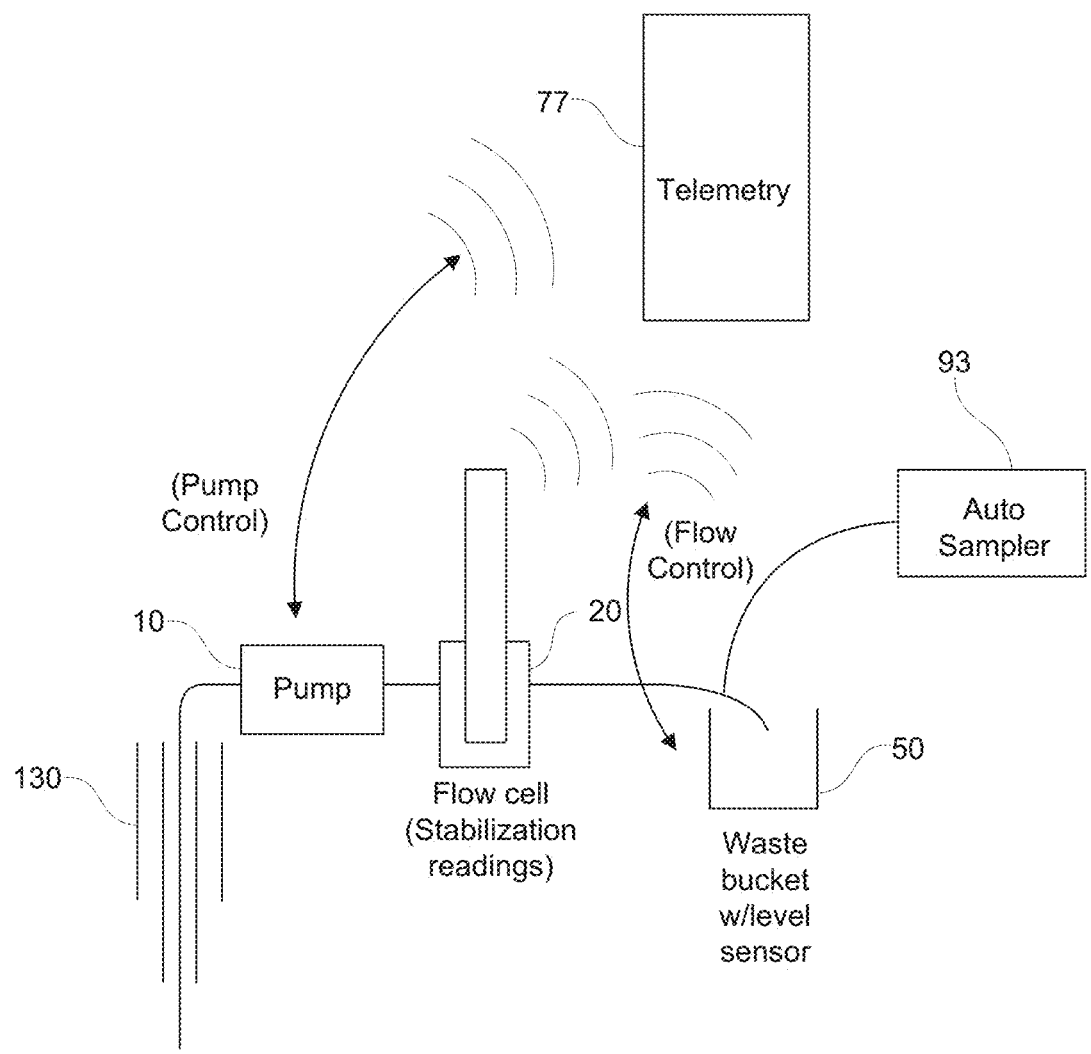
FIG. 3 is a schematic illustration of a low flow groundwater fluid sampling system with autosampler and telemetry.

FIGS. 1-3 are schematic overviews of a system for automation of low-flow groundwater fluid sampling. Low flow pump 10 pumps fluid 200, such as groundwater that has entered and been collected in a well 130 as indicated by arrows 201, to a flow cell 20. The system optionally includes a separate flow sensor 30. Well 130 may be a monitoring well for monitoring possible contamination of groundwater. The flow cell 20 is in fluid and electronic communication with the low flow pump 10. In this manner, the measured parameters by the flow cell may be used to, in turn, control pump, thereby establishing a feedback control. The flow cell 20 may have one or more fluid quality sensors 40 for measuring one or more fluid parameters. The flow cell may have an inlet port 22 for delivering fluid to the flow cell and outlet port 24 for removal of fluid from the flow cell. Valves 26 may be used to control flow of fluid to either waste container 50 or to fluid sample container 80, including a fluid sample container that is part of an autosampler 100 for automatically collecting samples for later pick up by an operator for transport to an off-site testing facility. A level sensor 60 may be positioned at a bottom surface 150 of the waste container 50 to provide an indication of the level of waste fluid 90 in the waste container. Any of the level sensors may use a pressure sensor to determine fluid height by P=ρgh (P is pressure, ρ is density, g is acceleration due to gravity, and h is fluid height). Furthermore, by measuring the change in the waste fluid level with time, the level sensor may itself be characterized as a flow sensor, where a plot of height versus time and the corresponding slope provides a measure of flow-rate, with adjustment to pump power made to maintain a relatively constant slope.

Communication device 70 is in wireless communication with many of the components, as illustrated by dashed arrows. As shown in FIGS. 2 and 3, communication device 70 may include a mobile device 75 and/or a telemetry system 77. The arrows are two-ended to reflect that not only is data provided to the device, but the device may be used to control the system, including pump flow-rate, sensor status, and any other component of interest, including valve 26 direction.

With respect to the well 130, a depth sensor 110 may be used to provide a measure of fluid depth in the well, thereby providing information about fluid drawdown level 120. The depth sensor 110 may be a pressure sensor. Sensor 110 may be in wireless communication with device 70 and/or pump 10, so that pump power or fluid flow-rate is adjusted so as to maintain an appropriate fluid depth, and maintain drawdown 120 at an acceptable level, or at least a constant level.

An "auto-calibrator" 140 may be incorporated into the system for automatically calibrating the sensors. The auto-calibrator may be provided as an adaptor that fluidically connects to the flow cell, such as via a controllable valve. One or more calibration solutions may be connected so that the calibration solution(s) are forced, including via a pump, into the cell and flushed out. The pumping force may be via the connected low flow pump or by a separate auto-calibrator pump. Waste solutions go to the waste bucket.

The flow cell 20 may be installed at an orientation angle that is not vertical (as shown in FIG. 1) and/or that is not horizontal, to prevent bubbles from forming on the sensor head. In another example (not shown in FIG. 1), the flow cell 20 may be installed at any orientation angle that is suitable for functioning according to design specifications in the system for automation of low-flow groundwater fluid sampling. The flow cell 20 has minimal volume within the cell, to allow for faster flow cell turnover and to minimize the volume of calibration solutions used, with an inlet port and an outlet port. The flow cell may be characterized as having an internal volume corresponding to the volume of liquid within the flow cell. The invention is compatible with a range of flow cell internal volumes, such as between 0.1 mL and 1 L, between 40 mL and 500 mL, and any sub-ranges thereof, with a preference for volumes as low as possible to provide faster flow cell turnover and efficiently utilize calibration solutions for the sensors.

The waste container may comprise a bucket with a level sensor or pressure transducer at or near the bucket bottom. The waste container is configured to allow waste flow to drop into the bucket with minimal surface disruption for more accurate readings. The bucket may have a constant diameter so that the pressure transducer is reliably calibrated to send a warning as to the need to empty the container of waste fluid and/or to decrease the flow through or stop the pump to avoid overflow of waste fluid. A top cover may be connected to the container to prevent spillage.

Figure 4:
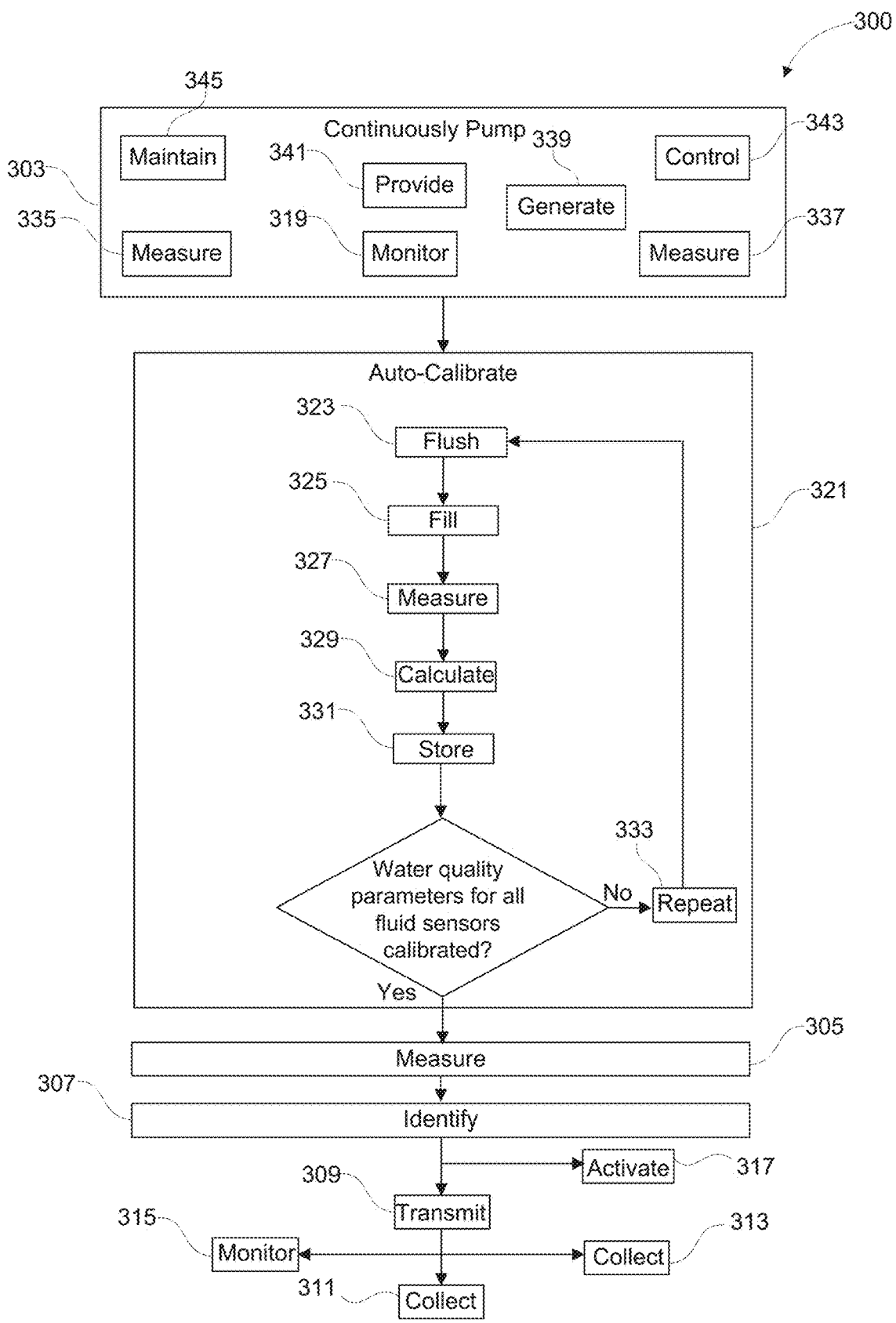
FIG. 4 is a flow chart illustration of a method for collecting fluid samples from groundwater.

FIG. 4 is a method 300 for collecting low flow fluid samples from groundwater. In an example, method 300 is implemented and/or performed, at least in part, using the systems shown and described with reference to FIGS. 1-3. Method 300 includes continuously pumping 303 a flow of groundwater fluid to a flow cell at a substantially constant flow-rate. Method 300 includes measuring 305 a fluid quality parameter time course with a fluid sensor in said flow cell. Method 300 includes identifying 307 a positive fluid quality stabilization status for the measured fluid quality parameter that reaches a steady-state value. Method 300 includes wirelessly transmitting 309 a signal to a communication device indicating a fluid sample is ready to be collected from said flow of groundwater fluid. In an example, method 300 includes manually collecting 311 the fluid sample.

In an example, method 300 includes collecting 313 waste fluid that exits said flow cell in a waste container, and monitoring 315 a waste fluid level with a level sensor connected to said waste container. In the example, method 300 optionally includes activating 317 an autosampler 100 to automatically collect fluid sample that exits said flow cell after the positive fluid quality stabilization status is identified 307.

In an example, the step of continuously pumping 303 is implemented and/or performed, at least in part, by a low-flow pump fluidly connected or in fluid contact with a sample well. In the example, the sample well is configured to monitor 319 contamination of ground water, including oil or gas contamination, heavy metal contamination, solvent contamination, or contamination of a material from an industrial process.

Method 300 optionally further includes the step of auto-calibrating 321 the fluid sensor before the measuring 305 step to ensure proper functioning of sensors in the flow cell. In the example, the auto-calibrating 321 step includes flushing 323 the flow cell with clean water. The auto-calibrating 321 step also includes filling 325 the flow cell with a calibration solution. The auto-calibrating 321 step further includes measuring 327 a calibration fluid quality parameter with the fluid sensor to ensure the sensor is calibrated, including over a range of calibration concentrations, to ensure accurate sensor readings before introduction of fluid sample. The auto-calibrating 321 step further includes calculating 329 a new calibration coefficient for the fluid sensor. The auto-calibrating 321 step also includes storing 331, in memory device(s), the new calibration coefficient for a subsequent fluid test measurement. The auto-calibrating 321 step further includes repeating 333 (e.g., iterating) through the auto-calibrating 321 step until all water quality parameters for all fluid sensors are calibrated.

In an example, the continuously pumping 303 step is automated or semi-automated by measuring 335 fluid flow through said flow cell and/or measuring 337 a fluid depth in a sample well. In the example, the measured 335 fluid flow and/or the measured 337 fluid depth generates 339 an output that is provided 341 as an input to the low flow pump to control pump power, thereby controlling 343 fluid flow in a feedback loop so as to maintain 345 a substantially constant flow-rate and/or fluid depth in the sample well.

In an example, method 300 is implemented and/or performed, at least in part, for simultaneous collection of low flow fluid samples from a plurality of wells with minimal active intervention by an operator.

Example 2: Groundwater Sampling System

Figure 5:
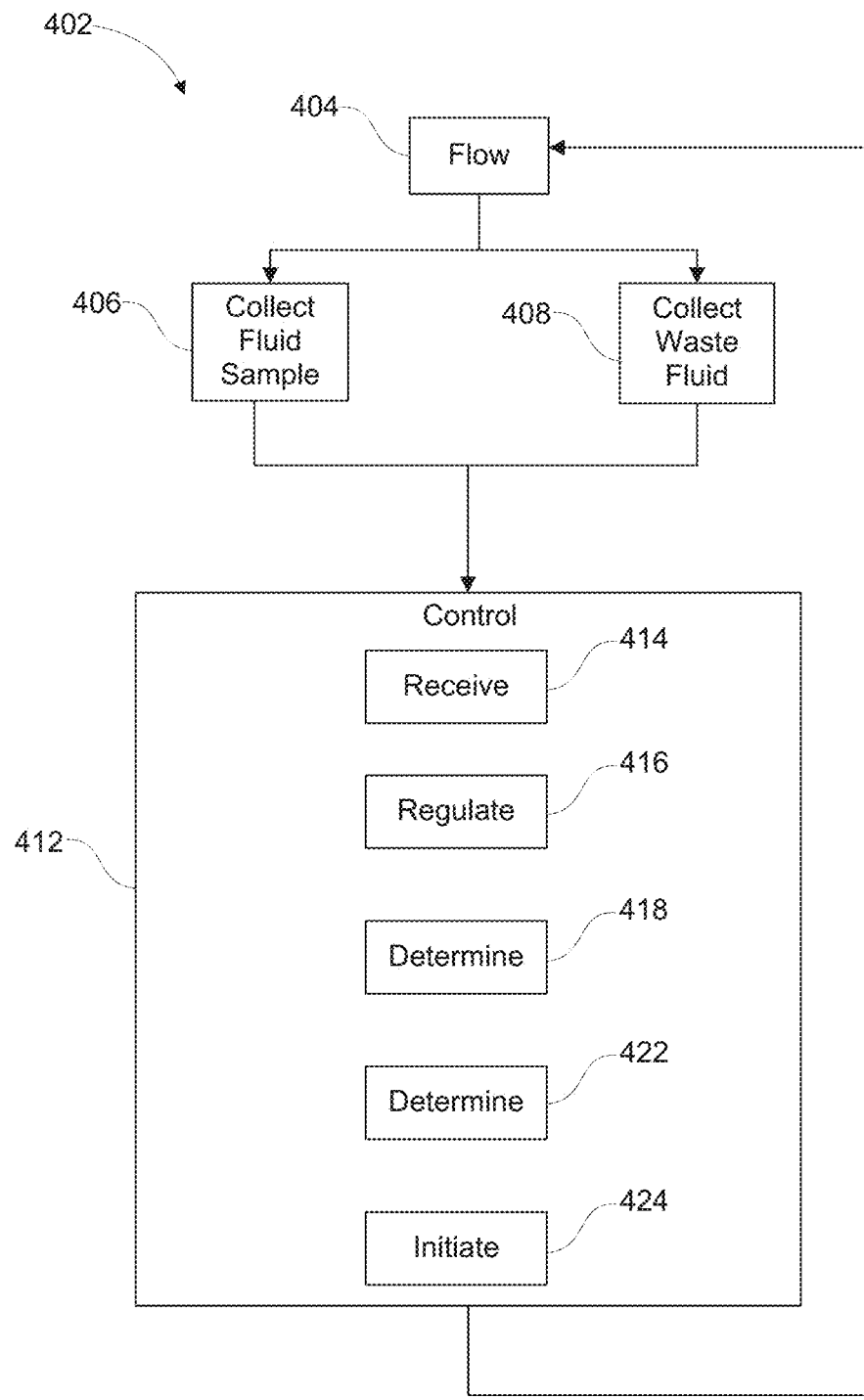
FIG. 5 is a flow chart illustration of a method for collecting fluid samples from groundwater according to another embodiment.
Figure 6:
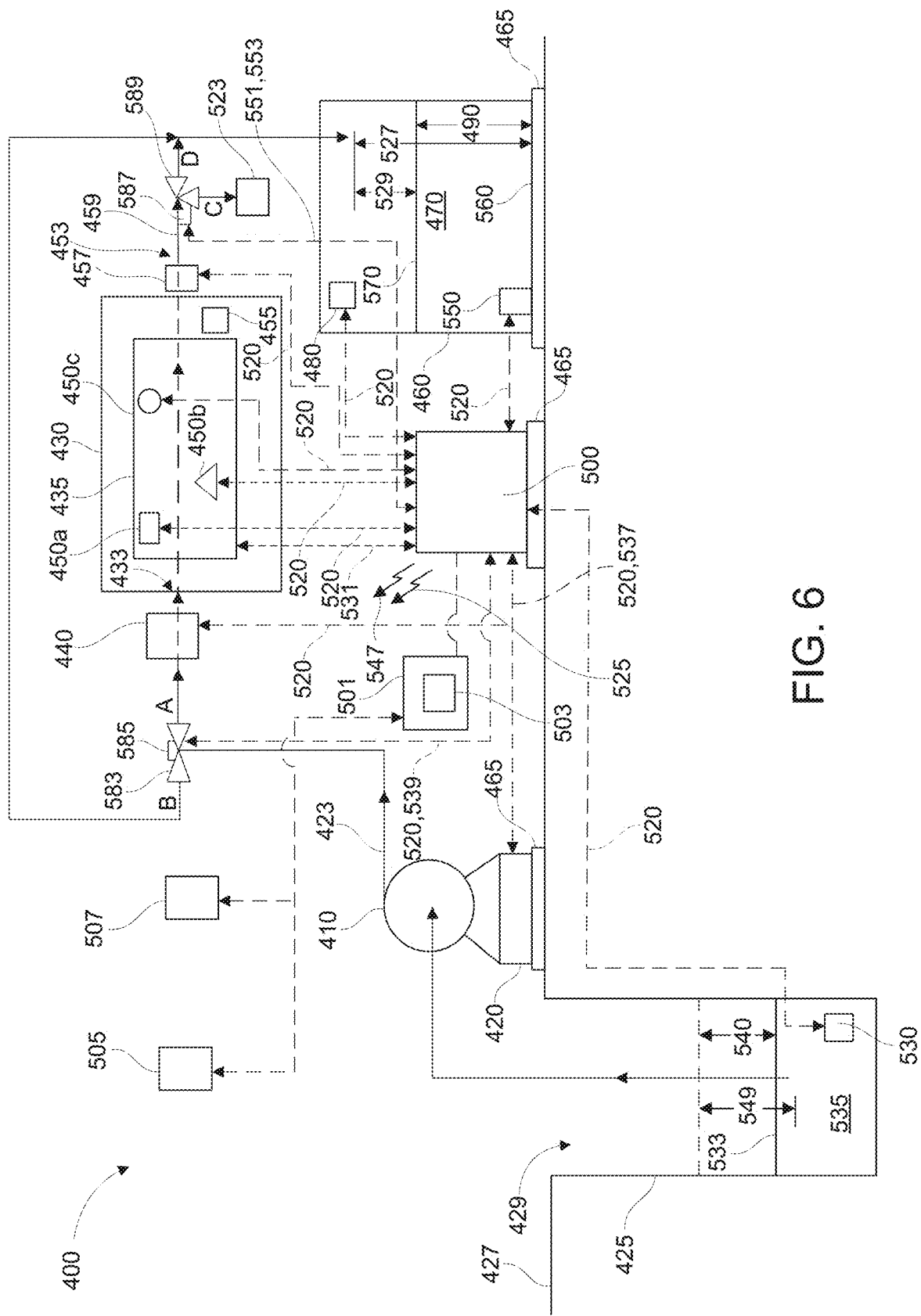
FIG. 6 is a schematic illustration of a groundwater sampling system according to another embodiment.
Figure 7:
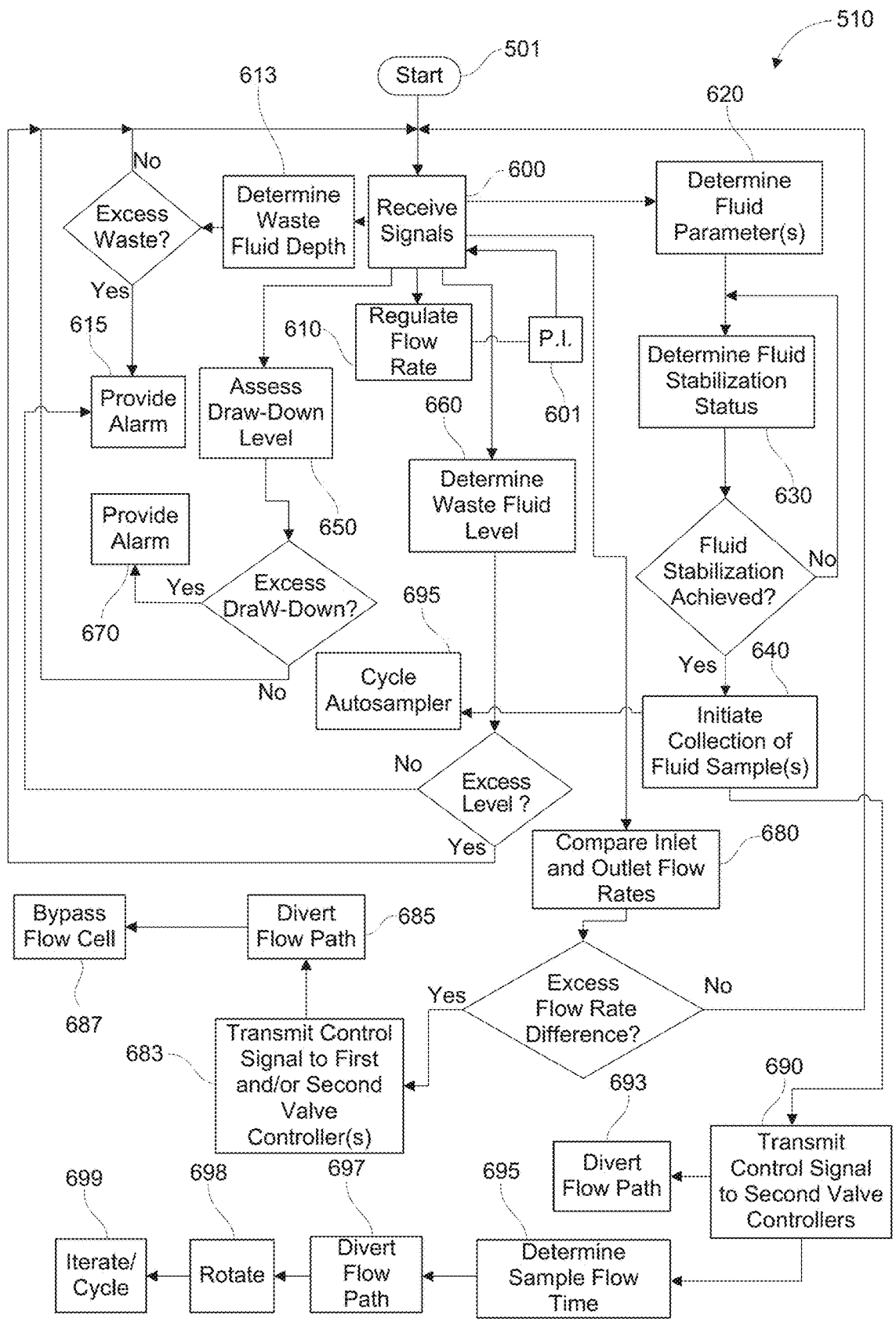
FIG. 7 is state diagram illustration of a control scheme for groundwater sampling.
Figure 8:
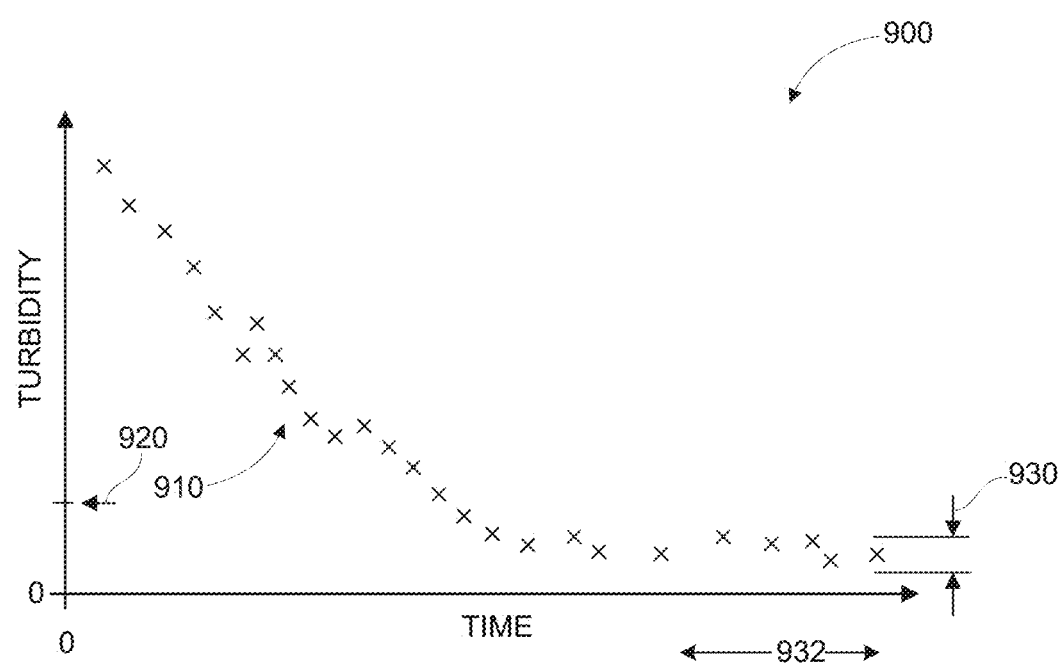
FIG. 8 is a plot illustrating an example of a fluid stabilization condition.

FIG. 5 is a method 402 for monitoring groundwater according to an embodiment of the disclosure. FIG. 6 is a schematic illustration of a groundwater sampling system 400 according to another embodiment of the disclosure. In an example, method 402 is implemented and/or performed, at least in part, using the system 400 shown in FIG. 6. FIG. 7 is state diagram of a control scheme 510 for groundwater sampling. FIG. 8 is a prophetic example of a fluid stabilization condition, as determined by a turbidity sensor. Initially, as the pump is engaged and liquid is pumped to the flow cell, there may be initially high turbidity, due to long-term build-up prior to testing. The sensor(s) can be used to evaluate when a type of steady-state is achieved, indicating the fluid sample is "clean", as determined by magnitude of deviation 930, such as a standard deviation or maximum deviation from an average over a certain number of fluid sample measurements or time period 932.

Referring to FIGS. 5 and 6, method 402 includes flowing 404, by at least one pump 410, groundwater 535 under test from a groundwater source (e.g., a monitoring well 425) to at least one flow cell 430. Pump(s) 410 include at least one pump controller 420. Flow cell(s) 430 includes one or more fluid quality sensors 450. Method 402 includes, for an output flow 459 of the groundwater 535 under test from the flow cell 430: collecting 406 a fluid sample 523 of the groundwater 535 under test; or collecting 408 a waste fluid 470 in at least one waste container 460. Waste container(s) 460 include level sensor(s) 480. Method 402 includes controlling 412, by a sampling controller 500, a groundwater monitoring system 400 used, at least in part, for implementing and/or performing method 402. Sampling controller 500 is communicatively coupled to pump controller(s) 420, flow sensor(s) 440, and sensors 480 (in waste container) and 530 (in well 429).

In method 402, the controlling 412 step includes receiving 414 signals 520 from pump controller(s) 420, fluid quality sensor(s) 450, and sensors 480 and 530. The controlling step 412 also includes regulating 416, based on the received signals 520, a flow-rate 423 to provide a desired or constant flow-rate to the flow cell 430. The controlling step 412 further includes determining 418, based on the received signals 520, one or more fluid parameters over a time course. The controlling step 412 also includes determining 422, based on the determined fluid parameter(s), a fluid stabilization status of groundwater 535 flowed to the flow cell 430 from the pump 410. The controlling 412 step further includes, in response to a fluid stabilization condition being determined, initiating 424 collection (e.g., by the collecting 406 step) of at least one fluid sample 523. In an example, method 402 is performed as a continuous or semi-continuous process, and the controlling 412 step is implemented for facilitating any or all of the aforementioned steps (e.g., flowing 404, collecting 406, and/or collecting 408 step(s)), and/or and any or all sub-steps thereof.

Referring to FIG. 6, system 400 includes a pump 410. In an example, pump 410 is a low flow pump 410. Pump 410 includes a pump controller 420 for regulating a fluid flow-rate 423 from a monitoring well 425 through the pump 410. In an example, pump 410 is positioned on a ground surface 427, including proximal an opening 429 of monitoring well 425. In another example (not shown in FIG. 6), pump 410 is positioned in the well 425 below the ground surface 427. System 400 includes a flow cell 430 in flow communication with the pump 410, and a flow sensor 440. In the example shown in FIG. 6, flow sensor 440 is positioned upstream of an inlet 433 of flow cell 430. In an example, flow sensor 440 is communicatively coupled to the pump controller 420 and/or a sampling controller 420. Flow cell 430 also includes one or more fluid quality sensors 450. Exemplary fluid quality sensor(s) 450 include one or more of: a turbidity sensor, a pressure sensor, a temperature sensor, a dissolved oxygen (DO) sensor, an electrical conductivity sensor, a pH sensor, an electrochemical sensor such as an oxidation reduction potential (ORP) sensor, and a fluorescence sensor. In an example, the flow cell 430 includes a plurality of fluid quality sensors 450 (e.g., first 450a, second 450b, and third 450c sensors). The sensor(s) 450 may be incorporated into a multi-parameter sonde 535, with at least the active sensing surfaces of the multi-parameter sonde 435 positioned in the flow cell 430. In an example, flow cell 430 includes an auto-calibrator 455 for automatically calibrating the fluid quality sensor(s) 450. System 400 includes a waste container 460 in flow communication with the flow cell 430 for collecting a waste fluid 470. In an example, waste container 460 is positioned on a ground pad 465, which providers a stable and protective weight bearing platform for container 460. Pump 410 and/or pump controller 420 may also be positioned on ground pad(s) 465 for similar purposes in system 400. The waste container 460 includes a level sensor 480 for measuring a waste fluid depth 490 in the waste container 460, including a pressure sensor to calculate fluid height in the container.

Referring to FIGS. 6 and 7, system 400 includes a sampling controller 500 communicatively coupled to pump controller 420, flow sensor 440, fluid quality sensor(s) 450, and sensors 480 and 530. In an example, system 400 includes a communication device 501 communicatively coupled to sampling controller 500. In an example, communication device 501 includes a telemetry system 503 positioned for and configured to transmitting and/or receiving data (e.g., encoded in sensor signals 520 and/or system 400 control signals) to a mobile device 505 and/or a remote monitoring station 507.

Sampling controller 500 implements a control scheme 510 for system 400 from a start state 501 (e.g., flow cell 430 awaiting flow of groundwater 535 under test to inlet 433 of flow cell 430). In implementing control scheme 510, sampling controller 500 receives 600 signals 520 from pump controller 420, flow sensor 440, fluid quality sensor(s) 450, and level sensor 480. In implementing control scheme 510, sampling controller 500 transmits a control signal 537 to pump controller 420 to facilitate regulating 610 the fluid flow-rate 423 of groundwater 535 from the pump 410 to the flow cell 430 based on the received signals 520 to provide and maintain a desired or constant flow-rate 423 to the flow cell 430. In an example, the desired or constant flow-rate 423 is greater than or equal to 1 mL/min and less than or equal to 500 mL/min (e.g., for a low flow pump 410). In an example, sampling controller 500 regulates 610 flow-rate 423 by implementing, including, without limitation, in conjunction with pump controller 420, proportional-integral (P.I.) feedback control 601.

In an example, flow-rate of groundwater 535 from pump 410 to flow cell 430 may be determined by sampling controller 500 based on the signal(s) 520 received from level 480 and/or depth 550 sensor(s) in the waste container 460. For instance, for a waste container 460 having known dimensions, a time rate of change in waste fluid 470 level and/or depth determined by sampling controller 500 is used thereby to determine the flow-rate, either instead of, or in addition to, based on the signal(s) 520 received from flow sensor 440 and/or output flow sensor 457.

For implementing control scheme 510 (FIG. 7), sampling controller 500 determines 613 waste fluid depth 490 in waste container 460 based on received signals 520 from a pressure transducer 550. In an example, sampling controller 500 provides 615 a waste fluid alarm 525 (e.g., including, without limitation, an audible and/or a visual alarm) in response to the measured waste fluid depth 490 in the waste container 460 being greater than or equal to a predetermined waste fluid depth 527 (e.g., excess waste). In an example (not shown in FIG. 7), in response to the determined 613 waste fluid depth 490 being greater than or equal to the predetermined waste fluid depth 527, sampling controller 500 transmits control signal 537 to pump controller 420 to facilitate stopping operation of pump(s) 410 or decreasing flow-rate 423, thereby automatically preventing waste overflow and attendant rick of contamination.

For implementing control scheme 510, sampling controller 500 determines 620 one or more fluid parameters over a time course based on the received signals 520, including, without limitation, from fluid quality sensor(s) (450). In implementing control scheme 510, sampling controller 500 determines 630 a fluid stabilization status of groundwater flowed to the flow cell 430 by the pump 410 based on the determined fluid parameter(s). In response to a fluid stabilization condition being determined 630 (e.g., fluid stabilization achieved), sampling controller 500 transmits a control signal 531 to flow cell 430 and/or to system 400 components associated with and/or connected to flow cell 430 to facilitate initiating 640 collection of at least one fluid sample 523 of the groundwater under test. In operation, all fluid (e.g., groundwater 535) provided to flow cell 430 is either collected in the fluid sample(s) 523 or is directed to waste container 460 and collected therein as waste fluid 470.

Referring to FIG. 8, a plot 900 is a prophetic example of a fluid parameter (y-axis, e.g., turbidity of groundwater 535 under test) stabilizing over a time course (x-axis, e.g., hours). A turbidity data set 910 generally decreases over the time course, with measured turbidity values eventually dropping below a user-predetermined value 920. In an example, for control scheme 510, sampling controller 500 determines 630 that the fluid stabilization condition is achieved when both: a user-predetermined number (e.g., a number greater than 1) of consecutive measured turbidity values in the data set 910 have values less than or equal to the predetermined value 920; and those consecutive measured values have a standard deviation about a mean value of less than a user-predetermined standard deviation value 930 or a maximum deviation from an average value over a certain number of sample values obtained over a time interval 932.

System 400 also includes a depth sensor 530 positioned in the monitoring well 425 (e.g., at least partially submerged under groundwater 535 surface 533). Depth sensor 530 is communicatively coupled to the sampling controller 500. In an example, for implementing control scheme 510, sampling controller 500 assesses 650 a fluid draw-down level 540 in the monitoring well 425 based on one or more signals 520 received from the depth sensor 530. In an example, sampling controller 500 provides 670 a draw-down alarm 527 in response to the assessed 650 draw-down level 540 in the monitoring well 425 being greater than or equal to a predetermined draw-down level 549 (e.g., excess draw down). In an example (not shown in FIG. 7), in response to the assessed 650 draw-down level 540 being greater than or equal to the predetermined draw-down level 549, sampling controller 500 transmits control signal 537 to pump controller 420 to facilitate stopping operation of pump(s) 410 or decreasing flow-rate 423.

System 400 further includes a pressure transducer 550 positioned at or near (e.g., proximal) a bottom surface 560 inside of the waste container 460 for measuring a depth of waste fluid 470 in the container 460. Pressure transducer 550 is communicatively coupled to the sampling controller 500. In an example, for implementing control scheme 510, sampling controller 500 determines 660 a waste fluid depth 470 in the waste container 460 based on one or more signals 520 received from the level sensor 480. In an example, sampling controller 500 provides 615 waste fluid alarm 525 in response to the determined 660 waste fluid depth 470 in the waste container 460 being greater than or equal to a predetermined waste depth value 529 (e.g., excess level). In an example (not shown in FIG. 7), in response to the determined 660 waste fluid depth 470 being greater than or equal to the predetermined waste depth 529, sampling controller 500 transmits control signal 537 to pump controller 420 to facilitate stopping operation of pump(s) 410 or decreasing flow-rate 423.

System 400 may include a first valve 583 having a first valve controller 585. In an example, first valve 583 is a first solenoid valve 583. First valve controller 585 is operatively coupled to first valve 583 and is communicatively coupled to sampling controller 500. First valve 583 is positioned upstream of the inlet 433 of flow cell 430. Under control of first valve controller 585, first valve 583 enables flow 423 to be alternately directed to one or two flow paths: (A) to inlet 433 of flow cell 430; and (B) to waste container 460.

System 400 may include a second valve 587 having a second valve controller 589. In an example, second valve 583 is a second solenoid valve 583. Second valve controller 589 is operatively coupled to second valve and is communicatively coupled to sampling controller 500. Second valve 587 is positioned downstream of an outlet 453 of flow cell 430. Under control of second valve controller 589, second valve 587 enables outlet flow 459 to be alternately directed to one or two flow paths: (C) to fluid sample collection 523; and (D) to waste container 460. Also, under control of second valve controller 589, second valve 587 alternately opens and closes to facilitate alternately starting and stopping, respectively, flow of groundwater into or out of outlet 453.

System 400 may further include an outlet flow sensor 457. In the example shown in FIG. 6, outlet flow sensor 457 is positioned downstream of outlet 453 of flow cell 430. In the example, outlet flow sensor 457 is positioned proximal outlet 453 of flow cell 430. Outlet flow sensor 457 is communicatively coupled to the sampling controller 500. In an example, for implementing control scheme 510, sampling controller 500 compares 680, based on signals 520 received from flow sensor 440 and from outlet flow sensor 457, a first flow-rate (e.g., flow-rate 423) into the inlet 433 of flow cell 430 to a second flow-rate (e.g., flow-rate 459) out of the outlet 453 of flow cell 430. In an example, sampling controller 500 subtracts a measured value of flow-rate 459 from a measured value of flow-rate 423. In the example, in response to a magnitude of a value of the difference between flow-rate 423 and flow-rate 459 being greater than or equal to a predetermined (e.g., predetermined by a system 400 user) flow-rate difference value (e.g., excess flow-rate difference), sampling controller 500 transmits 683 a control signal 539 to first valve controller 585 to facilitate diverting 685, by first valve 583, the pumped flow of the groundwater 435 under test from flow path A to flow path B. Diverting flow 423 from flow path A to flow path B bypasses 687 flow cell 430. In an example, the value of the difference between flow-rate 423 and flow-rate 459 being greater than or equal to the predetermined flow-rate difference value is indicative of an operational problem in system 400 requiring attention by user(s) thereof, such as an obstruction to fluid flow in the flow cell 430.

In an example, in response to the magnitude of the value of the difference between flow-rate 423 and flow-rate 459 being greater than or equal to the predetermined flow-rate difference value, sampling controller 500 transmits 683 a control signal 553 to second valve controller 589 to facilitate closing second valve 587 and ceasing flow 459 so that back flow (e.g., via flow path D) into the outlet 453 of flow cell 430 does not occur. In an example (not shown in FIG. 7), in response to the magnitude of a value of the difference between flow-rate 423 and flow-rate 459 being greater than or equal to the predetermined flow-rate difference value, sampling controller 500 transmits 683 control signal 537 to pump controller 420 to facilitate stopping operation of pump(s) 410 or decreasing flow-rate 423. In an example (not shown in FIG. 7), in response to the magnitude of a value of the difference between flow-rate 423 and flow-rate 459 being greater than or equal to the predetermined flow-rate difference value, sampling controller 500 provides a flow-rate alarm (e.g., including, without limitation, an audible and/or a visual alarm).

For implementing control scheme 510, initiating 640 collection of fluid sample(s) 523 includes, in response to the fluid stabilization condition being determined 630 (e.g., fluid stabilization achieved), sampling controller 500 transmits 690 a control signal 551 to second valve controller 589 to facilitate diverting 693, by second valve 587, the pumped flow (e.g., flow 459) of groundwater 435 under test from flow path D to flow path C. This diverting 693 of flow 459 further facilitates the collecting 406 step of method 402.

Figure 9:
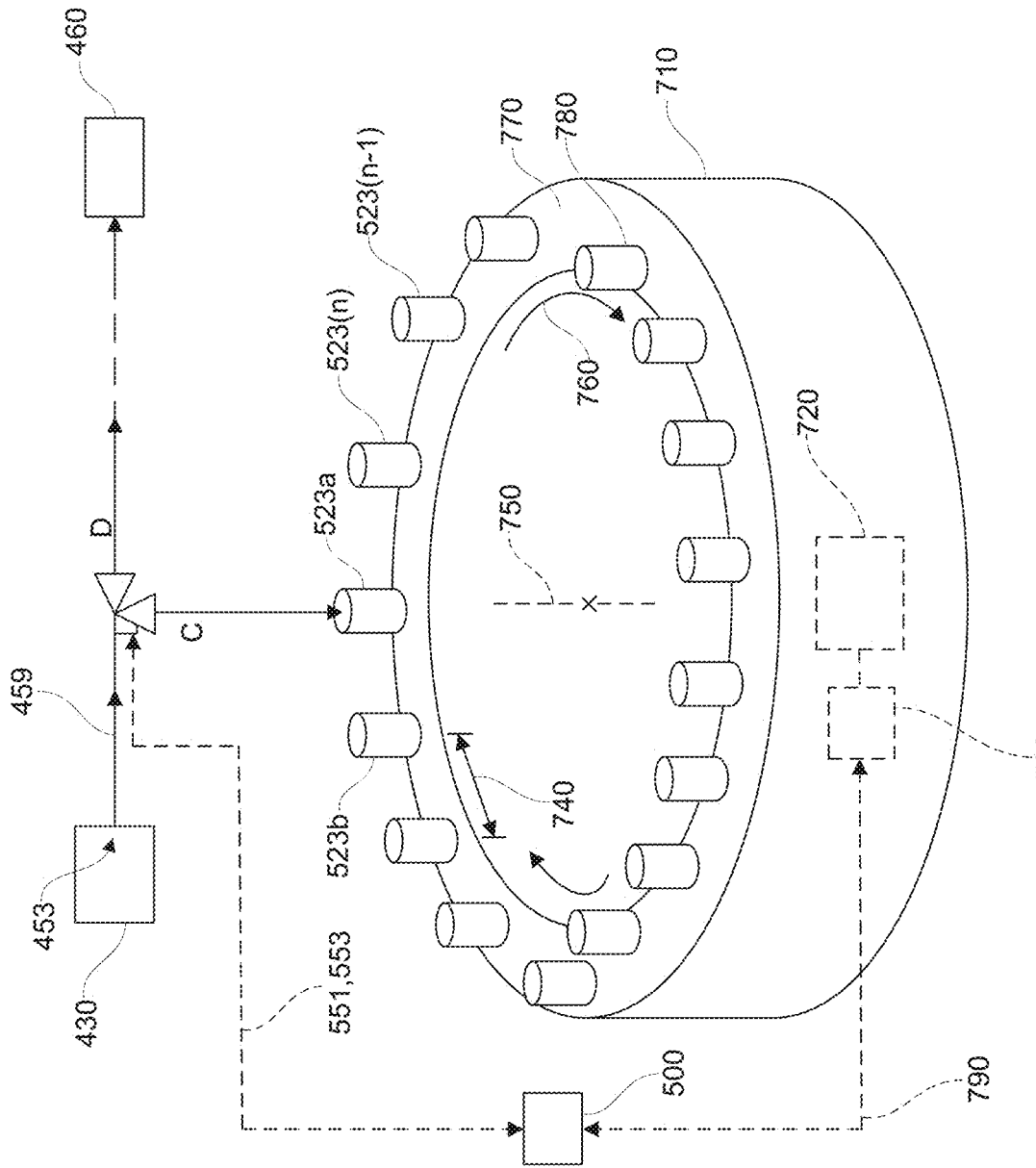
FIG. 9 is a schematic illustration of an autosampler.

FIG. 9 is a schematic diagram of system 400 including an autosampler 710. Referring to FIGS. 5-10, in an example, autosampler 710 includes an electric motor 720. In an example, motor 720 is a stepper motor 720. Autosampler 710 includes a motor controller 730 coupled to motor 720. Motor controller 730 is communicatively coupled to sampling controller 500. Autosampler 710 includes a sample platform 770 for holding a plurality of sample containers 780 (e.g., vials) for collecting and containing a plurality of fluid samples 523 (e.g., first 523*a*, second 523*b*, . . . , (n-1)-th, and (n)-th samples 523), including, without limitation, over the time course. To increment sample collection between each of the plurality of containers 780, motor 720 incrementally moves sample platform 770 (e.g., rotates in either a clockwise 760 or counterclockwise direction about a center axis 750 by a predetermined arc length 740).

In an example, upon sampling controller 500 initiating 650 collection of fluid samples 523, groundwater 535 under test enters a first container 780 via flow path C and is filled with first fluid sample 523*a*. Sampling controller 500 facilitates flow of first sample 523*a* into the first container 780 for a predetermined amount of time. Sampling controller 500 determines 695 the predetermined amount of time (e.g., sample flow time) based on the flow-rate 459, the available volume of first container 780, and the desired volume of first sample 523*a* to be collected. Substantially simultaneously with the start of the predetermined amount of time, sampling controller 500 facilitates, via second valve controller 489, diverting 693 flow 459 from flow path D to flow path C, thereby enabling collection of first fluid sample 523*a* into the first container 780. Substantially simultaneously with the conclusion of the predetermined amount of time, sampling controller 500 facilitates, via second valve controller 489, diverting 697 flow 459 from flow path C to flow path D, thereby stopping collection of first fluid sample 523*a* into the first container 780. Also, at or after the conclusion of the predetermined amount of time, sampling controller 500 facilitates, via motor controller 730 receiving a motor control signal 790 from controller 500, rotating 698 the sample 770 by the predetermined arc length 740. Sampling controller 500 iterates 699 through process steps associated with autosampler 710 for at least one iteration, based on the number (n) of fluid samples 523 to be collected.

In any or all of the examples described above with reference to system 400, system 400 components that transmit and/or receive data (e.g., sensor signals 520 and/or system 400 control signals) may be wirelessly communicatively coupled to each other including, without limitation, using Bluetooth®, WiFi, Zigbee, and/or like wireless communication protocol(s) known to persons skilled in the art. In any or all of the examples described above with reference to system 400, system 400 components that transmit and/or receive data (e.g., sensor signals 520 and/or system 400 control signals) may be communicatively coupled via wired connections including, without limitation, using serial, Ethernet, and/or like wired communication protocol(s) known to persons having skill in the art. In any or all of the examples described above with reference to system 400, system 400 components that transmit and/or receive data (e.g., sensor signals 520 and/or system 400 control signals) may be communicatively coupled to each other using both of, or combinations of, wireless and wired communication protocols.

Figure 10:
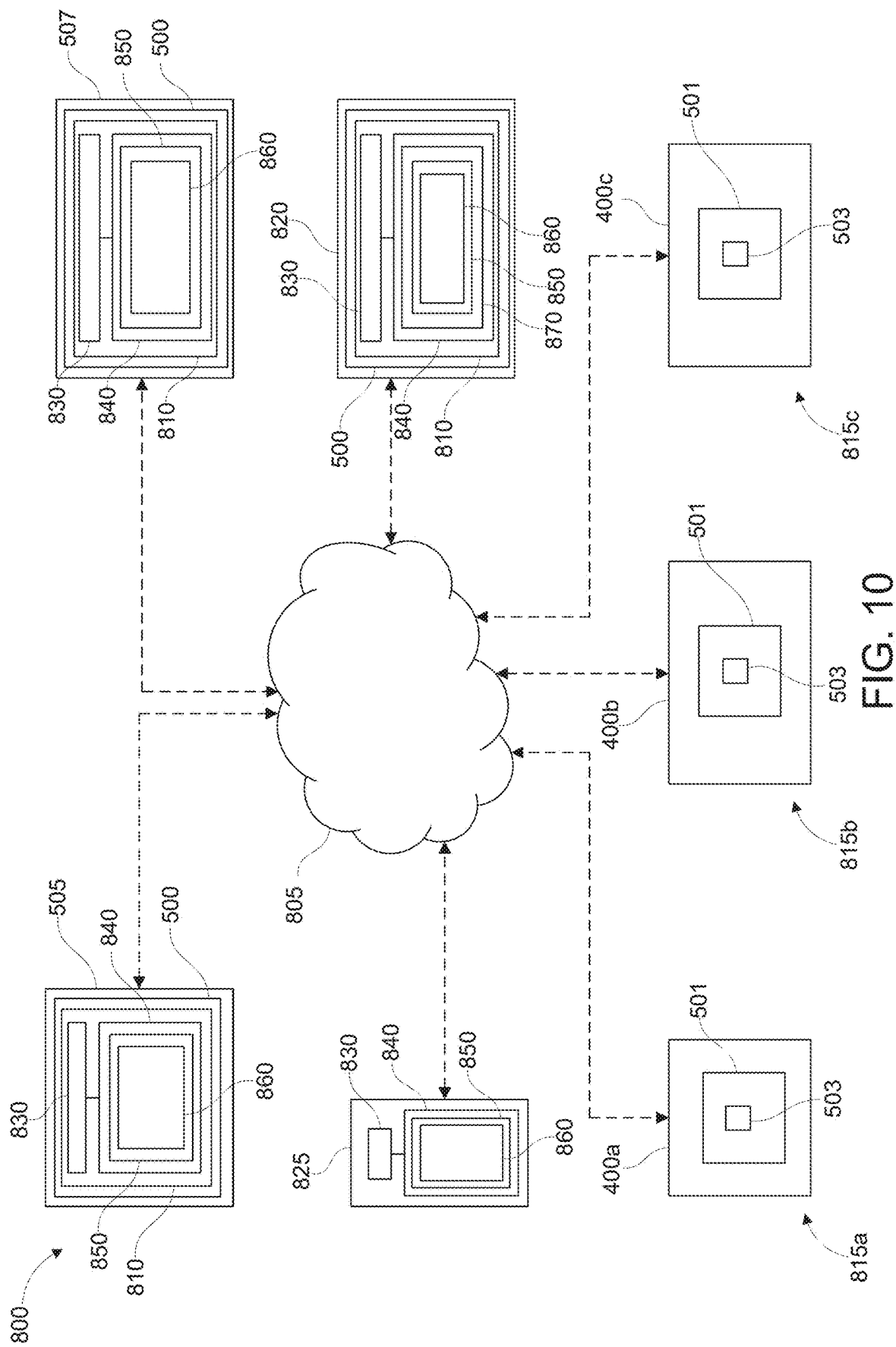
FIG. 10 is a schematic illustration of a networked computing environment for implementing any of the disclosed systems and methods for groundwater sampling.

FIG. 10 is a schematic illustration of a networked computing environment for implementing the disclosed systems and methods for groundwater 535 sampling. In an example, system 400 includes at least one computing device 810 communicatively coupled to one or more deployments of system 400 (e.g., via telemetry system 503 of system 400 and a transceiver of computing device 810, not shown in FIG. 10) in one or more deployment locations 815 (e.g., first 815*a*, second 815*b*, and third 815*c* deployment locations) through a network 805 (e.g., the Internet, an intranet, and/or a cellular network). Telemetry system 503 and/or communication device 501 transmits and receives data (e.g., sensor signals 520 and/or system 400 control signals) to and from, respectively, the computing device (810). The computing device(s) include one or more of mobile device 505, remote monitoring station 507, a mobile smart phone 820, and at least one server 825.

In an example, system 400 is part of a multiplexed groundwater monitoring system 800. Multiplexed system 800 includes a plurality of groundwater sampling systems 400 (e.g., first 400*a*, second 400*b*, and third 400*c* systems 400) for simultaneously monitoring of a plurality of groundwater sources (e.g., monitoring wells 425). Multiplexed system 800 may be implemented and/or deployed over a geographic area of any size, including, without limitation, utilizing Internet of Things (IoT) protocols, standards, and practices.

Computing device(s) 810 include one or more processors 830 communicatively coupled to one or more memory devices 840 (collectively referred to herein as memory 840. Memory 840 stores including, without limitation, by reading, writing, and/or deleting, data associated with operation of system(s) 400. In an example, memory 840 includes a non-transitory computer readable medium 850 which stores processor 830-executable instructions encoded as software 860 or firmware. When executed by the processor(s), the processor 830-executable instructions cause the processor(s) 830 to execute processor 830 and memory 840 operations that facilitate implementing the control scheme 510 in system(s) 400, as shown and described above with reference to FIGS. 5-9. In examples of system 400 and/or system 800 where computing device 810 is a mobile smart phone 820, memory 840 thereof includes an app 870. In such embodiments, the app 870 includes the non-transitory computer readable medium 850. In an example, computing device(s) 810 implement and/or perform, at least in part, the functionality of sampling controller(s) 420 in system(s) 400 and/or system 800, either instead of, or in addition to, sampling controller(s) 420 resident at or near location(s) 815 of groundwater 535 source(s) (e.g., monitoring well(s) 425).

In an example, system(s) 400 and/or multiplexed system 800 is/are used in a groundwater 535 contamination monitoring and/or remediation application(s). In such embodiments, collected (e.g., in the collecting 406 step of method 402) fluid sample(s) 523 is/are used for off-site testing of the fluid sample(s) 523. In an example, system(s) 400 and/or multiplexed system 800 is/are used for monitoring and/or remediation application(s) for oil, gas, and/or chemical facilities and/or sources of actual or potential groundwater 535 contamination. In such embodiments, where the above described components of system 400 are positioned in proximity to flammable materials and/or chemicals, such component(s) are selected and/or installed in accordance with "explosion proof" standards so as to comply with application construction codes and/or related laws and regulations.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a temperature range, a flow range, a number range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A low flow groundwater fluid sampling system comprising:
   a low flow pump having a pump power;
   a flow cell in fluid communication with said low flow pump, wherein said flow cell comprises one or more fluid quality sensors;
   a flow sensor to control said pump power so as to maintain a desired flow-rate through the flow cell;
   a communication device in wireless communication with each of said low flow pump, flow cell and flow sensor, wherein:
      said low flow pump has an adjustable pump power to provide a desired constant flow-rate to said flow cell from an electronic communication between said low flow pump and said flow sensor, and said at least one fluid quality sensor measures one or more fluid parameters over a time course to assess a fluid stabilization status;

upon fluid stabilization said communication device indicates an affirmative fluid stabilization condition and that a fluid sample may be collected.

2. The system of claim 1, wherein said flow sensor comprises a waste container and a level sensor operably connected to the waste container, wherein the waste container is in fluid communication with said flow cell for collecting a waste fluid.

3. The system of claim 2, wherein said waste container level sensor comprises a pressure transducer at a bottom surface of said waste container to measure waste fluid level in said waste container.

4. The system of claim 1, further comprising a waste container in fluid communication with said flow cell for collecting a waste fluid from said flow cell.

5. The system of claim 1, further comprising an autosampler in fluid communication with said flow cell, wherein an output flow from said flow cell for said affirmative fluid stabilization condition is directed to said autosampler for collection.

6. The system of claim 1, wherein said fluid quality sensors are selected from the group consisting of: a turbidity sensor, a pressure sensor, a temperature sensor, an electrical conductivity sensor, a pH sensor, an electrochemical sensor such as an oxidation reduction potential (ORP) sensor, a fluorescence sensor, and any combination thereof.

7. The system of claim 1, wherein said flow cell further comprises an auto-calibrator for automatically calibrating said one or more fluid quality sensors.

8. The system of claim 1, wherein said desired or constant flow-rate is greater than or equal to 1 mL/min and less than or equal to 500 mL/min.

9. The system of claim 1, wherein one or more of a fluid flow-rate or a water well depth is transmitted to said communication device and a control signal is transmitted from said communication device to said low flow pump to maintain the desired or constant fluid flow-rate and/or a water well depth.

10. The system of claim 1, wherein said communication device comprises a mobile smartphone.

11. The system of claim 1, wherein said communication device comprises a telemetry system positioned for transmitting data to a mobile device or a remote monitoring station.

12. The system of claim 1 that is part of a multiplexed system comprising a plurality of said low flow groundwater sampling systems for simultaneously monitoring of a plurality groundwater wells.

13. A method for collecting low flow fluid samples from groundwater, the method comprising the steps of:

continuously pumping a flow of groundwater fluid to a flow cell at a substantially constant flow-rate;

measuring a flow-rate through the flow cell and controlling a pump power based on the measured flow-rate so as to maintain the substantially constant flow-rate through the flow cell;

measuring a fluid quality parameter time course with a fluid sensor in said flow cell;

identifying a positive fluid quality stabilization status for said measured fluid quality parameter that reaches a steady-state value; and wirelessly transmitting a signal to a communication device indicating a fluid sample is ready to be collected from said flow of groundwater fluid.

14. The method of claim 13, further comprising the step of manually collecting said fluid sample.

15. The method of claim 13, wherein the measuring the flow rate comprises the steps of:

collecting a waste fluid that exits said flow cell in a waste container; and monitoring a waste fluid level with a level sensor connected to said waste container.

16. The method of claim 15, further comprising the step of: activating an autosampler to automatically collect fluid sample that exits said flow cell after said positive fluid quality stabilization status is identified.

17. The method of claim 13 for simultaneous collection of a plurality of low flow fluid samples from a plurality of wells.

18. The method of claim 13, wherein said continuously pumping is by a low-flow pump fluidly connected to a sample well or in fluid contact with a sample well.

19. The method of claim 18, wherein said sample well is configured to monitor contamination of ground water, including oil or gas contamination, heavy metal contamination, solvent contamination, or contamination of a material from an industrial process.

20. The method of claim 13, further comprising the step of auto-calibrating said fluid sensor before said measuring step by:

flushing the flow cell with clean water;

filling the flow cell with a calibration solution;

measuring a calibration fluid quality parameter with the fluid sensor until stability is reached;

calculating a new calibration coefficient for the fluid sensor;

storing the new calibration coefficient for a subsequent fluid test measurement; and repeating until all water quality parameters for all fluid sensors are calibrated.

21. The method of claim 13, further comprising measuring a fluid depth in a sample well, wherein the fluid depth generates an output that is provided as an input to said low flow pump to control pump power, thereby controlling a fluid depth in said sample well.

* * * * *